United States Patent
Vogels et al.

(10) Patent No.: US 6,187,710 B1
(45) Date of Patent: Feb. 13, 2001

(54) SYNTHETIC SWELLING CLAY MINERALS

(76) Inventors: Roland Jacobus Martinus Josephus Vogels, Reitdiepstraat 75/la, 3522 GG Utrecht; John Wilhelm Geus, Gezichtslaan 100, 3723 GJ Bilthoven, both of (NL)

(*) Notice: Under 35 U.S.C. 154(b), the term of this patent shall be extended for 0 days.

(21) Appl. No.: 08/793,684

(22) PCT Filed: Aug. 31, 1995

(86) PCT No.: PCT/NL95/00295

§ 371 Date: Nov. 10, 1997

§ 102(e) Date: Nov. 10, 1997

(87) PCT Pub. No.: WO96/07613

PCT Pub. Date: Mar. 14, 1996

(30) Foreign Application Priority Data

Sep. 2, 1994 (NL) .................................................. 9401433

(51) Int. Cl.[7] .................................................. B01J 21/16
(52) U.S. Cl. .............................. 502/80; 502/63; 502/84; 502/263
(58) Field of Search ................................ 502/63, 80, 84, 502/263

(56) References Cited

U.S. PATENT DOCUMENTS

| 3,252,889 | * | 5/1966 | Capell et al. ............... 502/263 |
| 3,666,407 | | 5/1972 | Orlemann ..................... 23/111 |
| 3,671,190 | | 6/1972 | Neumann ..................... 23/111 |
| 3,852,405 | | 12/1974 | Granquist ................... 423/118 |
| 4,113,658 | | 9/1978 | Geus ......................... 252/454 |
| 4,176,090 | * | 11/1979 | Vaughan et al. ............. 502/84 |
| 4,216,188 | | 8/1980 | Shabrai et al. ............. 423/118 |
| 4,248,739 | | 2/1981 | Vaughan et al. .......... 252/455 R |
| 4,271,043 | | 6/1981 | Vaughan et al. .......... 252/455 R |
| 5,503,819 | * | 4/1996 | Holmgren ................... 502/63 |

FOREIGN PATENT DOCUMENTS

| 0225659 | 11/1986 | (EP) . |
| 9213637 | 8/1992 | (WO) . |
| WO 92/13637 | * 8/1992 | (WO) . |

OTHER PUBLICATIONS

Reviews in Mineralogy; vol. 19; Hydrous Phyllosilicates, (1988), S. W. Bailery, ed.
Sciences Géologiques, Synthese et Cristallogenese des Smectites (1983), A. Decarreau (and partial translation).

* cited by examiner

Primary Examiner—David W. Wu
Assistant Examiner—Ling-Siu Choi
(74) Attorney, Agent, or Firm—Weingarten, Schurgin, Gagnebin & Hayes LLP

(57) ABSTRACT

Synthetic clay minerals are made up of elementary three-layer platelets consisting of a central layer of octahedrally oxygen-surrounded metal ions (octahedron layer), which is surrounded by two tetrahedrally surrounded, silicon atom-containing layers (tetrahedron layers), a number of such elementary platelets being optionally stacked. The dimensions of the clay platelets vary from 0.01 $\mu$m to 1 $\mu$m, the number of the stacked elementary three-layer platelets varies from on average one platelet to twenty platelets, while in the octahedron layer at most 30 at. % of the metal ions has been replaced by ions of a lower valency and in the tetrahedron layers at most 15 at. % of the silicon ions has been replaced by ions of a lower valency, such a replacement having taken place in at least one of these layers and these layers having a deficiency of positive charge because of the replacement. They are prepared by bringing the pH of an aqueous liquid containing the components of the clay to a value of 3–9 and the temperature of the liquid to a value of from 60 to 350° C. and maintaining it at said value for the time required for the reaction, the pH being maintained at a value within said range.

39 Claims, 1 Drawing Sheet

XRD of Examples 6 through 9

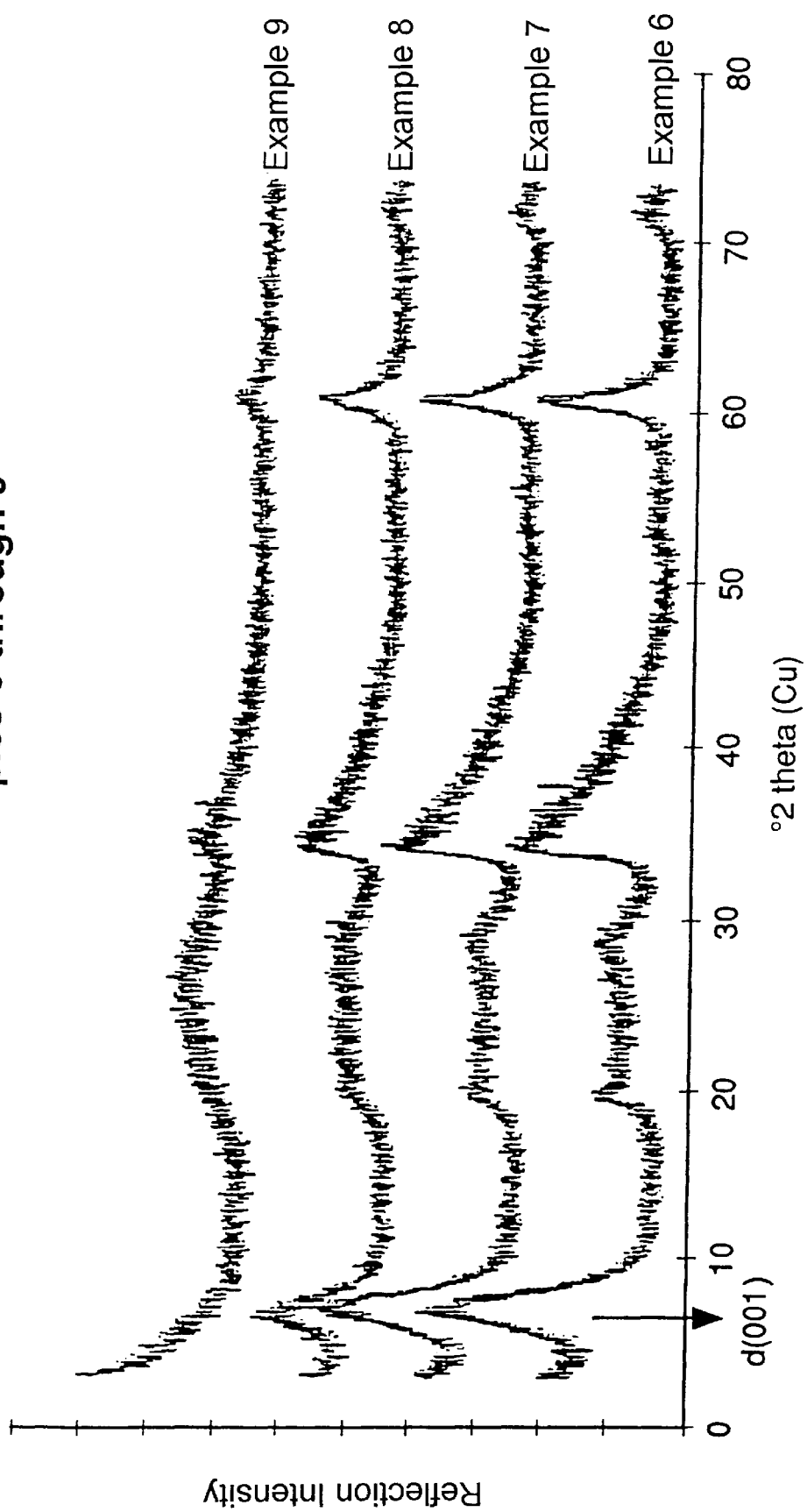

SYNTHETIC SWELLING CLAY MINERALS

BACKGROUND OF THE INVENTION

The invention relates to new, synthetic swelling clay minerals, as well as to a process for the preparation of such clay minerals.

Clay minerals are solid substances, substantially made up of metal and oxygen atoms, whose crystal lattice has a layered structure. This layered structure consists of three repeating layers. Located centrally in this elementary three-layer structure is a layer of substantially trivalent or substantially divalent metal ions (cations). Examples of clay minerals with substantially trivalent ions are montmorillonite and beidellite; examples of clay minerals with substantially divalent ions are hectorite and saponite. The metal ions present in the central layer are octahedrally surrounded by oxygen and hydroxyl ions. In a clay mineral with trivalent ions, two of the three octahedron positions are occupied by metal ions. Accordingly, this is referred to as a di-octahedral clay mineral. In a clay mineral with divalent metal ions, all three octahedron positions are occupied by metal ions; this is referred to as a tri-octahedral clay mineral. On opposite sides of this layer of octahedrally surrounded metal ions occurs a layer of tetrahedrally surrounded ions. These tetrahedrally surrounded ions are generally silicon ions, while a part of the silicon can optionally be replaced by germanium. The unit of the tetrahedrally surrounded silicon ions is $Si_2O_5(OH)$. In this connection it is noted that in the tetrahedron and octahedron layers the actual point where the charge is located cannot always be indicated equally clearly. The term 'ions' as used in this context accordingly relates to the situation where an atom, given a completely ionic structure, should possess an electrostatic charge corresponding with the oxidation state.

Essential to clay minerals is that a part of the cations present are substituted by ions of a lower valency. Thus it is possible to substitute a part of the trivalent or divalent metal ions in the octahedron layer by divalent and monovalent metal ions, respectively. With substantially trivalent metal ions, this substitution results in montmorillonite and with substantially divalent metal ions in hectorite. It is also possible to substitute the tetravalent silicon ions in the tetrahedron layers by trivalent aluminum ions. With a clay mineral with almost exclusively trivalent ions in the octahedron layer, the result is then a beidellite and with a clay mineral having almost exclusively divalent ions in the octahedron layer, the result is a saponite. Of course, substitution by an ion of lower valency leads to a deficiency of positive charge of the platelets. This deficiency of positive charge is compensated by including cations between the platelets. Generally, these cations are included in hydrated form, which leads to the swelling of the clay. The distances between the three-layer platelets is increased by the inclusion of the hydrated cations. This capacity to swell by incorporating hydrated cations is characteristic of clay minerals.

If no metal ions or silicon ions are substituted by ions of a lower valency, the platelets are not charged. The mineral then does not absorb any water into the interlayer and therefore does not swell. The mineral with exclusively aluminum in the octahedron layer and silicon in the tetrahedron layer is pyrophyllite and the mineral with exclusively magnesium in the octahedron layer and silicon in the tetrahedron layer is talc. The swelling clay minerals having a negative charge of from 0.2 to 0.6 per unit cell, $-O_{10}(OH)_2$, are known as smectites.

The cations in the interlayer of swollen clay minerals are strongly hydrated. As a result, these ions are mobile and can be readily exchanged. The exchange is carried out by suspending the clay mineral in a concentrated solution of the cation to be provided in the interlayer. The high concentration provides for a concentration gradient as a result of which the exchange proceeds. Upon completion of the exchange, the concentrated solution is removed by filtration or, preferably, by centrifugation and washing, whereafter, if necessary, the last metal ions not bound in the interlayer can be removed by dialysis.

The negative charge of the platelets can be compensated not only with hydrated cations, but also with (hydrated) hydrogen ions, $H_3O^+$. In this case the clay can function as a solid acid, which leads to important catalytic applications. Suspending a clay mineral in a concentrated acid does not lead without more to the provision of hydrogen ions in the interlayer. In fact, it has been found that the acid reacts with the cations of the clay structure, so that these ions are removed from the clay structure. These cations eventually end up in interlayer positions.

If it is desired to provide Brønsted-acid groups in a hydrated clay mineral, in general hydrolysing metal ions are provided in the interlayer. As a result of the hydrolysis, hydrogen ions are formed. Upon reduction of the amount of water in the interlayer, for instance through thermal desorption, the acid strength increases. Due to the lesser amount of water, the residual water molecules are polarised more strongly by the metal ions. Upon complete removal of the water, however, the Brønsted-acid groups disappear. If it is desired to impart Brønsted-acid properties to clay minerals at elevated temperatures, (hydrated) ammonium ions can be provided in the interlayer. Upon heating, the water and the ammonia escape while a proton remains behind.

Natural clay minerals have long been used for the practice of catalytic reactions in liquid and in gaseous phase. In general, the catalytic activity of clay minerals is based on the presence of Brønsted- or Lewis-acid groups in the clay minerals. In the conventional acid-catalysed reactions in the liquid phase often sulfuric acid is used. This acid yields Brønsted-acid groups while, moreover, it can dehydrate in that it has strong water-binding properties, and can take up undesired higher molecular by-products. What results, however, are large amounts of polluted sulfuric acid, acid tar, for which it is difficult to find any use. Neutralisation of large amounts of sulfuric acid used as catalyst leads to ammonium sulfate, which can be disposed of as less high-grade fertilizer, which is useful only for a business which also produces and/or sells other kinds of fertilizer.

In syntheses where Lewis-acid catalysts are needed, such as the Friedel-Crafts synthesis, metal chlorides, such as aluminum chloride, are used as catalyst. Hydrolysis of the aluminum chloride upon completion of the reaction leads to large amounts of highly corrosive suspensions of aluminum hydroxide.

Accordingly, both the use of sulfuric acid and the use of Lewis-acid catalysts, such as aluminum chloride or zinc chloride, entail drawbacks. Therefore, there is a need for solid acid catalysts that are suitable for carrying out such acid-catalysed reactions. Accordingly, one of the objects of the invention is to provide such solid acid catalysts for carrying out reactions in the liquid and/or gaseous phase, which are catalysed by Brønsted- and/or Lewis-acids.

Of great importance in this connection is the degree of hydration of the clay minerals. If water-immiscible, liquid reactants are to be processed, the presence of water on the surface of clay minerals prevents the required intensive contact between the reactants and the clay surface. The water will preferentially wet the clay surface. In many liquid phase reactions, therefore, it will be necessary to priorly dehydrate the clay mineral to be used. This must take place without any substantial reduction of the accessible clay surface. Also, the reagents used will generally have to be dried to a far-reaching extent.

Another important problem with the use of solid catalysts in liquid phase reactions is the separation of the catalyst from the reaction mixture. Generally, this is effected by filtration or centrifugation. The known, mostly natural, clay minerals generally lead to a compressible filter cake. This makes it cumbersome to separate the clay mineral by filtration or centrifugation from the reaction products and unreacted reactants. One of the tasks of the invention is therefore to provide clay minerals in a form which is readily separable from the reaction products and unreacted reactants.

Another problem occurring in catalytic reactions in the presence of heterogeneous catalysts relates to the occurrence of transport impediments in the porous catalyst body. In the liquid phase diffusion coefficients are generally a factor $10^4$ lower than in the gaseous phase. As a result, soon transport impediments arise when high-porosity solid catalysts are used in liquid phase reactions. Especially in organo-chemical reactions transport impediments have a highly adverse effect on the selectivity. Thus, it will be desired, when alkylating benzene for instance, to minimize the amounts of di- or tri-substituted reaction products. This is possible only when reactants and reaction products are quickly transported through the solid catalyst. This requires a catalyst with short and wide pores. A third task of the invention is thus to provide clay minerals with short, wide pores which can be readily separated from a liquid phase.

In summary, clay minerals for use as liquid phase catalysts should satisfy the following, partly contradictory, requirements:

(i) a far-reaching dehydration must be possible without a substantial reduction of the active surface accessible to reactants, (ii) ready separation of the liquid phase in which the reaction has been carried out, (iii) excellent transport properties, that is, the presence of wide, short pores; short pores require small catalyst bodies, which renders the separation from the liquid phase more difficult again.

In the gaseous phase clay minerals were used especially for catalytically cracking petroleum fractions. By the end of the thirties, natural clays were used on a large scale in the catalytic cracking of petroleum fractions. Soon, however, clay minerals were replaced by amorphous aluminum oxide-silicon dioxide catalysts, which were found to satisfy better the requirements of the technical implementation of the cracking process. By spray-drying, on the basis of amorphous aluminum oxide-silicon dioxide, wear-resistant bodies of dimensions of from 50 to 200 $\mu$m could be easily produced. These bodies are simple to transport in a gas stream from the regeneration zone to the cracking zone.

Subsequently, in the sixties, cracking catalysts based on zeolites were developed, which exhibited a higher activity and selectivity. From natural clays, bodies of the required dimensions can be prepared which contain only zeolite crystallites. In general, however, small zeolite crystallites (approximately 1 $\mu$m or less) are included in amorphous aluminum oxide-silicon dioxide, which functions as binder.

The limited dimensions of the pores in zeolites have as a consequence that heavier fractions can no longer be cracked with zeolites.

The elementary platelets of current, natural clay minerals are relatively large, >1 to 30 $\mu$m, while mostly a large number of platelets, viz. more than 20 to 50 elementary platelets, are stacked into packages. As a result, upon dehydration, which renders the interlayer inaccessible, the catalytically active surface is relatively small. Is has now been found that the accessible surface of dehydrated clay minerals can be markedly enlarged by 'pillaring' the clay mineral. In that case, by metal ion-exchange hydrated oligomers or polymers of inter alia aluminum, zirconium, titanium and/or chromium are provided between the clay layers. Upon dehydration, a metal oxide 'pillar' is left. After dehydration, the distance between the clay layers varies from 0.6 to 1.6 nm. It is endeavored to realise even greater distances between the clay layers by arranging greater pillars. This is to make it possible to process heavier petroleum fractions.

Especially around 1980, much research was done on the pillars of clay minerals, as appears from the number of patent applications filed and the number of patents granted. An example is U.S. Pat. No. 4,176,090, which discloses pillared clay materials that are useful as catalysts and sorbents. According to this patent specification, an aqueous suspension of a natural clay mineral, such as calcium bentonite or beidellite, is prepared and the suspension is mixed with a solution of polymeric metal (hydr)oxide particles. The positively charged polymeric complexes exchange with the cations originally present in the clay. Then the clay is separated from the aqueous solution, the material is dried, and finally calcination is carried out at a temperature of about 200 to 700° C. While initially the interlayer is completely filled with water, in which the originally present cations or the polymeric complexes occur, after drying and calcination only the oxide of the polymeric complex is present. The greater part of the interlayer is now accessible to gas molecules since the elementary clay layers are kept separate by the oxide formed from the polymeric complex. As appears from the examples included in the patent specification, half an hour is sufficient to complete the exchange in the aqueous suspension. It should be noted here that in the examples relatively small clay particles are used, viz. less than about 2 $\mu$m. This appears from Example 3 of the above U.S. Pat. No. 4,176,090; in fact, it is communicated that the separation of the clay particles from the aqueous phase poses problems. For this reason, in that example a flocculating agent is used. For this purpose, inter alia a sodium silicate solution can be used.

Mentioned as pillaring agents are positively charged hydroxy complexes of aluminum, zirconium, and/or titanium. In one of these examples, a mixed hydroxy complex of magnesium and aluminum is prepared. In most examples of the above U.S. Pat. No. 4,176,090 pillaring is carried out with polymers based on hydrated aluminum oxide. It is possible to prepare discrete complexes with thirteen aluminum ions, the so-called $Al_{13}$ complex. However, it is difficult to obtain this complex in pure form; nearly always a considerable part of the aluminum is present in the system in a different form, while the strongly diluted solutions of $Al_{13}$ generally necessitate large volumes of water. For the preparation of pillared clay minerals on a technical scale, this is a disadvantage.

The distance of the elementary platelets in the clay structure, which is easy to determine by X-ray diffraction, is 0.7 to 1.0 nm after pillaring and after calcination. The BET surface varies from 150 to 600 m² per gram and the pore volume from 0.1 to 0.6 ml per gram. Further, it is found that more than 50% of the surface and in many cases even more than 75% of the surface is present in pores of a size less than 3 nm. This means that the elementary platelets of the clay structure are stacked to a considerable extent. If the elementary platelets were arranged relatively arbitrarily, as in a house of cards, a much larger fraction of the surface should occur in much wider pores.

U.S. Pat. No. 4,216,188 relates to the preparation of pillared clay minerals from bentonite (montmorillonite). Here, polymeric hydroxy complexes of aluminum and chromium are mentioned as reagents for obtaining the pillars. The process of this patent distinguishes over that of U.S. Pat. No. 4,176,090 in that now the colloidal suspension of the starting clay mineral is prepared more carefully. The clay mineral is suspended in water and by treatment with NaCl the interlayer ions originally present are exchanged for sodium. Then the suspension is washed thoroughly and the last residues of NaCl are removed by dialyses. By centrifugation, the particles of less than 2 $\mu$m are then separated. Next, the suspended clay particles are reacted with the polymeric aluminum or chromium complex, with the concentration of the chromium complex in particular being very low. After a thermal treatment at 150 to 450° C. a BET surface of 160 to 240 m² per gram is obtained. This patent mentions a distance between the elementary platelets of about 0.9 nm.

U.S. Pat. No. 4,248,739 describes a method wherein the pillars are provided using positively charged hydroxy complexes having a molecular weight of from 2000 to 20,000. However, the properties of the calcined pillared clay minerals are not significantly different from those mentioned in U.S. Pat. No. 4,176,090. The methods for the preparation of pillared clay minerals mentioned in U.S. Pat. No. 4,271,043 are not essentially different, either. Although the specification mentions that the thermal stability of the pillared clay minerals is high.

If form-selective catalytic reactions are to be carried out, a catalyst of narrowly defined pore dimensions is required. Zeolites satisfy this requirement exellently. However, a problem is that the transport in zeolites often proceeds poorly. Thus it has been demonstrated that molecules cannot pass each other in the pores of zeolites. Pillaring clay minerals also leads to pores of sharply limited dimensions, so that such materials can be suitable heterogeneous catalysts for such reactions. One condition, however, is that the materials can be prepared on a technical scale in a well reproducible manner.

Now, the preparation of suitable pillaring agents, such as the polymeric hydroxy complexes on a technical scale is difficult. In general, there are only a few businesses that produce suitable solutions of these complexes. In addition, in most cases the fraction of the aluminum that is present as $Al_{13}$ is not large. As a consequence, very large volumes have to be employed to produce large amounts of pillared clay minerals, which in general is technically very difficult. Accordingly, one of the objects of the invention is to provide processes for the production of suitable pillaring agents on an industrial scale. Since the provision of the hydrated pillars in the clay mineral does not pose any problems technically, provided the clay particles are not too large, the production of the hydrated pillars on a technical scale seems to be the chief problem.

Purifying natural clays is cumbersome. In general, the clay must be suspended and the impurities allowed to settle. Then the clay must be separated from the suspension, which is technically problematic. This appeared hereinabove in the discussion of U.S. Pat. No. 4,176,090, which publication mentioned that much leakage of clay particles through the filter occurred. In addition, there is the problem that important clay minerals do not occur in nature or do so to an insufficient extent. One of the major problems in the use of natural clay minerals for catalytic purposes is moreover that although these materials may be very cheap, the properties are very difficult to control.

The synthesis of clay minerals according to the current state of the art is technically difficult. Customarily, a protracted (a few weeks) hydrothermal treatment is used at relatively high temperatures and pressures, under agitation of the aqueous suspension. In general, only a few grams or even only some tens of milligrams of a clay mineral can be synthesized simultaneously. The application of this technology on a large (industrial) scale is very difficult, if not impossible. As a result, synthetic clay minerals are costly. An example of such a synthesis, in this case of hectorite, is given in U.S. Pat. No. 3,666,407. Because hectorite has especially interesting rheological properties and does not occur much in nature, the synthesis of this mineral is of interest. This preparation starts from natural talc, which contains magnesium, oxygen and silicon and which occurs amply in nature in pure form. This material, after being crushed and mixed with lithium carbonate, is heated at 760 to 980° C. for approximately 1 hour. After cooling, water glass and soda are added and for 8 to 16 hours the mixture thus obtained is treated hydrothermally, i.e. at high temperature and high pressure, under agitation of the preparation. It is clear that this is a relatively costly preparative procedure.

This also applies to the method for the preparation of synthetic clay minerals discussed in U.S. Pat. No. 3,671,190. In this patent it is observed that the preparative procedures thus far known have only been carried out on a laboratory scale and often yield only milligrams of the desired clay mineral which moreover is often polluted with quarts. In the method of U.S. Pat. No. 3,671,190, magnesium and silicon are coprecipitated by mixing water glass with a solution of a magnesium salt. The suspension thus obtained is then treated hydrothermally. To that end, the mixture is maintained under pressure at 250° C. for about 4 hours with stirring. It is difficult to control the degree of crystallization and hence the dimensions of the crystallites.

Owing to the poorly controllable properties of natural clay minerals and the high price of synthetic clay minerals, the use of clay minerals for catalytic purposes has remained quite limited. Although the patent literature around 1980 evidenced much research effort in the field of the catalysis of (pillared) clay minerals, the technical application thereof has remained very slight.

Surprisingly, it has now been found that the above-mentioned tasks can be fulfilled by making use of clay minerals of which the dimensions of clay platelets are controllably variable from 1 $\mu$m to 0.05 $\mu$m, the stacking of elementary platelets can be controlled from on average one to three platelets to a number of approximately twenty platelets, while the ratio of different metal ions in the octahedron layer and/or tetrahedron layer is adjustable.

BRIEF DESCRIPTION OF THE FIGURE

FIG. 1. Reduction of reflection intensities in the 001 plane [d (001)] as determined by x-ray diffraction (XRD) from example 6 to example 9.

Accordingly, the invention therefore relates in a first embodiment to clay minerals made up of elementary three-layer platelets consisting of a central layer of octahedrally oxygen-surrounded metal ions (octahedron layer), which layer is surrounded by two tetrahedrally surrounded, silicon atom-containing layers (tetrahedron layers), and a number of such elementary platelets being optionally stacked, characterized in that the dimensions of the clay platelets vary from 0.01 µm to 1 µm, the number of the stacked elementary three-layer platelets varies from one platelet to on average twenty platelets, while in the octahedron layer at most 30 at. % of the metal ions has been replaced by ions of a lower valency and in the tetrahedron layers at most 15 at. % of the silicon ions has been replaced by ions of a lower valency, such a replacement having taken place in at least one of these layers and these layers having a deficiency of positive charge because of the replacement.

This deficiency of positive charge is compensated by protons and/or cations which are present between the platelets. According to the invention, it is essential that at least a part of the octahedrally and/or the tetrahedrally surrounded ions have been replaced by other ions of lower valency. In a first embodiment, the trivalent ions in the octahedron layer can be replaced by divalent ions. If the octahedron layer is made up of divalent ions, a part thereof can be replaced by lithium ions.

In a second embodiment, the silicon (germanium) in the tetrahedron layer can be replaced by trivalent ions. It is also possible to have a replacement in the octahedron layer as well as in the tetrahedron layer. In the case where a clay mineral is synthetized with an octahedron layer based on divalent ions and with a substitution of trivalent ions in the tetrahedron layer, a slight substitution of trivalent ions may also occur in the octahedron layer. However, the net charge of the elementary platelets will always be negative, i.e. there is a deficiency of positive charge in the platelets.

In this connection, it is observed that the term 'replacement' or 'substitution' is employed in the meaning that a change has occurred relative to the ideal structure. After all, typically, in practice both components (ions of higher and lower valency) will simultaneously be presented during the preparation of the clay minerals.

In the octahedron layer, aluminum, chromium, iron(III), cobalt(III), manganese(III), gallium, vanadium, molybdenum, tungsten, indium, rhodium and/or scandium are preferably present as trivalent ions.

As divalent ions, magnesium, zinc, nickel, cobalt(II), iron(II), manganese(II), and/or beryllium are preferably present in the octahedron layer. This may be the component of the higher valency as well as the component of the lower valency.

In the tetrahedron layer, silicon and/or germanium is present as tetravalent component and preferably aluminum, boron, gallium, chromium, iron(III), cobalt(III) and/or manganese(III) are present as trivalent component.

A part of the hydroxyl groups present in the platelets can partly be replaced by fluorine.

For processing heavier petroleum fractions, catalysts having pores of at least 6 nm are preferably used. For the time being, this seems hard to achieve by means of the pillaring of clay materials. For this reason, a following objective of the invention is to provide clay minerals having, in a dehydrated state, a large and properly accessible surface. Efforts are directed to having the active surface present in wide pores of a dimension of at least 6 nm. One of the objectives of the invention is the preparation of clay minerals in such a manner that the elementary platelets are hardly mutually stacked, but form a house of cards, as it were. Such a house of cards-stucture is characterized by the presence of wide pores having a pore size of at least 6 nm, determined by means of nitrogen sorption at 77K, as described by S. J. Gregg & K. S. W. Sing in 'Adsorption, Surface Area and Porisity, *Academic Press London*, New York (1967) and/or in K. S. W. Sing, 'Characterization of CAtalysts' (J. M. Thomas and R. M. Lambert eds), pp. 11–29, *John Wiley & Sons, Chichester* (1980).

Such a structure has the property that hardly any (001) or no reflections occur in the X-ray diffraction pattern, which indicates that hardly any stacking is present. In addition, this appears from the fact that the larger part of the accessible surface area, more in particular more than 150 $m^2/g$, occurs in pores wider than 6 nm.

The preparation of the synthetic clay minerals according to the invention proves to be surprisingly simple. In the widest sense, one may argue that the components required for the synthesis, oxides of silicon (germanium) for the tetrahedron layer and the tri/di/monovalent ions for the octahedron layer, are presented in aqueous medium, are brought to the desired pH (3–9, preferably 5–9) and are then maintained for some time at a temperature of 60–350° C., with the pH being maintained within the desired range. The reaction time strongly depends on temperature, and hence on pressure, with higher temperatures enabling shorter reaction times. In practice, reaction times to the order of 5–25 hours are found at the lower temperatures, 60–125° C., whereas at temperatures in the range of 150° C. and higher, reaction times to the order of some minutes to approximately 2.5 hours may suffice. The reaction time partly determines the dimensions of the clay minerals.

Such a process can be carried out in a number of manners, depending on the nature of the components and the desired result. Preferably, chlorides of the metals involved are not worked with, as they lead to a reaction into clay minerals that is hardly perceptible, if at all.

In accordance with a first variant, the starting products for the preparation are mixed as a solution and the pH is adjusted to the range where the preparation is to take place. During the following heating operation, the pH is kept substantially constant, for instance through hydrolysis of urea, injection of a neutralizing agent below the surface of the well-stirred liquid, or with electrochemical means.

However, for achieving a rapid and proper preparation, it is preferred to homogeneously increase the pH of a solution of the metal ions to be incorporated into the octahedron layer in the presence of solid silicon dioxide. For this, an acid solution of the components is started from, which is for instance obtained by mixing water glass and aluminate with each other, acidifying it and adding a solution of a nickel salt thereto. The pH should be kept low enough for the nickel not to precipitate. Then, the pH is increased homogeneously, for instance through hydrolysis of urea, injection of a neutralizing agent below the surface of the vigorously stirred liquid, or with electrochemical means.

It is also possible to start from a suspension of finely divided silicon dioxide or silica gel in a solution of the metal ions to be incorporated into the octahedron layer. The metals are then preferably precipitated by increasing the pH homogeneously. It is also possible to carry out this process in the presence of a thin layer of silicon oxide provided on a solid surface, for instance on the walls of the channels of a monolith or on the surface of a stirrer. At an increasing pH of the liquid, the metal ions react with the silicon dioxide to form silicate structures. For this preparation no high pressures are required; it is possible to operate under atmospheric pressure, while scaling up of the process is extremely simple, because a homogeneous solution of the metal ions to be incorporated is worked from.

Surprisingly, it has been found that in the presence of two different metal ions, these metal ions are incorporated into the octahedron layer side by side. The typical swelling clay structure is brought about by the presence of divalent and trivalent ions side by side in the octahedron layer.

The temperature at which the pH is homogeneously increased influences the dimensions of the clay platelets formed. At higher temperatures, larger clay platelets are formed. In accordance with the invention, the dimensions of the elementary clay platelets are hence set by selecting the temperature and the time of the preparation at the proper values. Generally, the temperature will be set between approximately 40 and 200° C. Of course, at temperatures above approximately 100° C. it is necessary to operate under pressure. A skilled person is able to determine the proper temperature and time through simple routine tests.

The stacking of the elementary clay platelets, i.e. the number of elementary three-layer systems, is determined by the ionic strength of the solution from which the precipitation takes place. At a higher ionic strength, which can be achieved through the addition of, for instance, sodium nitrate, the elementaire clay platelets are stacked more. Without limiting the scope of the invention, it is assumed that reduction of the thickness of the electrostatic double layer around the clay platelets by the higher ionic strength decreases the mutual repulsion of the clay platelets. In accordance with the invention, the stacking of the elementary clay platelets is therefore controlled by setting the ionic strength of the solution wherein the reaction resulting in the clay minerals is carried out.

In accordance with a preferred embodiment of the invention, synthetic clay minerals are prepared at a low ionic strength of the solution. This may for instance by achieved by increasing the pH through the hydrolysis of urea. During the hydrolysis of urea, carbon dioxide escapes from the suspension, while the dissociation of ammonia is limited and ammonia escapes at higher pH levels. For this reason, ammonia can also be injected below the surface of the suspension. In these cases, a synthetic clay mineral results wherein the orientation of the elementary platelets is analogous with a house of cards. Hence, the stacking of the platelets is slight. In that case, a synthetic clay mineral is obtained having a high surface area present in wide pores. In particular, a clay having a surface area of at least 150 m² per gram mainly present in pores of at least 6 nm belongs to the invention.

If it is desired to prepare, through the pillaring of clay minerals, pores of narrowly defined dimensions, clay minerals are required of which the elementary platelets are stacked to a large extent, at least 10 elementary three-layer platelets. This requires operating at a high ionic strength of the solution. If one wishes to increase the pH value of the suspension homogeneously, according to the invention, the disproportionation of sodium nitrite can advantageously be used. Sodium nitrite reacts according to

$$3NaNO_2 + H_2O = NaNO_3 + 2NO + 2NaOH$$

The pH value of the suspension rises because of the release of sodium hydroxide. Of course, the reaction should be caused to proceed in the absence of oxygen (air) to prevent oxidation of the NO. After oxidation to $NO_2$, it reacts to form nitric acid and NO, as a result of which the pH decreases. Because no reactants escape in a gaseous form, the ionic strength in this case remains high, so that the elementary clay platelets are stacked to a large extent. Also, through injection of sodium hydroxide or other alkaline solutions below the surface of the suspension, the pH value can be increased homogeneously. However, in that case, it is more difficult to prevent inhomogeneities in the suspension on an industrial scale.

Further, incorporation of substantially zinc ions into the octahedron layer has proved to result in much larger elementary platelets than incorporation of substantially magnesium ions. The dimension of the elementary platelets of clay minerals having substantially zinc ions in the octahedron layer is approximately 0.1–0.2 μm, whereas the corresponding dimension in the case of substantially magnesium ions in the octahedron layer-is only 0.02 μm. Surprisingly, it has now appeared that in the presence of zinc ions and magnesium ions in the solution, both being present in the solution as divalent ions, these ions are incorporated into the octahedron layer side by side. The dimensions of the elementary clay platelets vary continuously with the zinc/magnesium ratio set, contrary to expectation, viz. the formation of a mixture of two clays, one on the basis of zinc and the other on the basis of magnesium. In acordance with the invention, the dimensions of the elementary clay layers are set within wider limits by setting the zinc/magnesium ratio.

The process of precipitating metal ions from homogeneous solution by increasing the pH of the solution in the presence of a suspended carrier material has priorly been proposed for the provision of a catalytically active precursor uniformly distributed over the surface of the carrier. This process is known as deposition precipitation. The procedure for providing catalytically active precursors on the surface of carriers suspended in the solution is described at length in U.S. Pat. No. 4,113,658 and in J. W. Geus 'Production and Thermal Pretreatment of Supported Catalysts' in 'Preparation of Catalysts III Scientific Bases for the Preparation of Heterogeneous Catalysts' (G. Poncelet, P. Grange and P. A. Jacobs eds.) pp. 1–33 *Elsevier Amsterdam* (1983). It was found that during deposition precipitation of in particular divalent metal ions, such as nickel and cobalt, reaction of suspended silicon dioxide occurs to form a hydrosilicate, a structure analogous with the structure of talc of garnierite. However, such structures do not exhibit any acid properties. This is caused by the fact that only divalent metal ions occur in the octahedron layer and only silicon ions occur in the tetrahedron layer, as a consequence of which the clay platelets do not have a negative charge.

The absence of acid properties of the above-mentioned structures with only nickel ions in the octahedron layer is known in literature. As a measure for the acid properties of the catalyst, the activity of the solid substance for cumene cracking is used. Granquist (W. T. Granquist, U.S. Pat. No. 3,852,405, 1974) determined the activity of nickel garnierite, the equivalent of talc with nickel ions instead of magnesium ions, for the cracking of cumene. See also Harold E. Swift in 'Advanced Materials in Catalysis' (James J. Burton and Robert L. Garten eds.) pp. 209–233 *Academic Press New York* (1977). He observed that no cumene was converted. The activity can therefore not be measured. On the other hand, a montmorillonite with nickel ions and aluminum ions exhibited under the same conditions a conversion of 84–100%. The montmorillonite was synthetically prepared under hydrothermal conditions. In view of these publications, it is surprising that during precipitation from homogeneous solution by increasing the pH in the presence of suspended silicon dioxide under atmospheric pressure at temperatures below 100° C., clay minerals are obtained with two metal ions from the aqueuos solution being incorporated into the structure side by side.

In general, substitution of silicon by aluminum in the tetrahedron layer results in stronger acid sites than substitution of metal ions of lower valency in the octahedron layer. The negative charge is then present closer to the surface of the clay platelets. Surprisingly, it has now been found that aluminum ions can be incorporated in an excellently controllable manner into the tetrahedron layer, where they replace silicon ions. In accordance with the invention, this can be effected by treating silicon dioxide with a basic aluminate solution, by setting, through acidification, the pH at such a level that the metal ions to be incorporated into the octahedron layer are still solluble, adding these metal ions, and then increasing the pH of the solution (homogeneously). In accordance with a preferred embodiment of this process according to the invention, a solution of water glass is started from to which a basic aluminate solution has been added. Then, this solution is acidified whereby the pH is reduced to a level at which the metal ions to be incorporated into the octahedron layer are soluble. After that, the pH of the liquid is increased homogeneously to create the desired clay mineral in insoluble form. Al MAS-NMR measurements show that a fraction of maximally 15 at% of the silicon ions can thus be replaced by aluminum ions. The aluminum is hardly incorporated, if at all, into the octahedron positions or at sites between the clay layers.

As observed hereinabove, it is an object of the invention to prepare synthetic clay minerals which can effectively and easily be separated from a liquid phase and which are characterized by the presence of short and wide pores. It is known that it is possible to provide a highly porous, continuous layer of silicon dioxide on solid substrates so as to be firmly bound. This process is described in International patent application WO-A 92/13637. In this process, a solution of silicone rubber, for instance in ethyl acetate, is started from, and a thin layer of that solution is provided on the desired solid substrate. In this connection, one may think of the walls of the channels of a monolith or of the surface of a stirrer, whereupon, through calcination, a homogeneous, continuous (i.e. practically crack-free) layer of silicon oxide is formed. Surprisingly, it has been found that the above-mentioned reaction in which from homogeneous solution, metal ions, including aluminate ions, react with suspended silicon dioxide, can also be carried out with the finely divided silicon dioxide provided on the solid surface. This process according to the invention results in clay platelets which are firmly connected to the solid surface. In accordance with a preferred embodiment of the process according to the invention, synthetic clay layers are provided on suitable solid surfaces in the above manner. Such clay layers, firmly bound to solid surfaces and having a controllable chemical composition and structure, also form part of the invention. In accordance with a preferred embodiment according to the invention, the clay layers are provided on the surface of the walls of the channels of monoliths, which are either made of ceramics or of metal, or on the surface area of stirrers.

This process enables providing relatively thin clay layers having wide pores on suitable solid substrates. The thickness of the clay layer determines the length of the pores, which is of great significance for the transport of reactants and reaction products in the clay structure. The thickness of the clay layer is 1–10 $\mu$m, preferably 1–5 $\mu$m, and more preferably 2–3 $\mu$m. Because of the stong bond to the solid surface, separation from the liquid is in this case no problem whatsoever. As the layer is thin, the pores are short, as a result of which no transport impediments occur, the less so because the pores of the clay layers thus provided are relatively wide. This is essential for the application of synthetic clay minerals for liquid phase reactions.

In accordance with another embodiment of the invention, elementary three-layer platelets of clay minerals according to the invention are provided on active carbon. Preferably, this takes place on carbon bodies having dimensions greater than 1 $\mu$m. By carrying out the synthesis of the clay minerals in a suspension of the active carbon, such products are obtained. Preferably, filamentary carbon is used, for instance obtained through the growth of carbon on small metal particles. Such carbon filaments have great strength and occur as balls having dimensions of approximately 3 $\mu$m. The accessible surface area of the filaments is approximately 200 m$^2$/g, which surface area is present in very wide pores. The clay minerals provided on the carbon have small dimensions, so that transport impediments do not occur, while a rapid and complete separation of the liquid phase is possible all the same.

For carrying out 'shape-selective' catalytic reactions, it is essential to have pillared clay minerals. Generally, the clay minerals will be synthesized at a high ionic strength of the solution, so that the elementary platelets are strongly stacked. In accordance with a special process according to the invention, the polymeric complexes for pillaring are now prepared by homogeneously increasing the pH of suitable solutions of metal ions, more in particular aluminum ions, for instance as described hereinabove. Preferably, the pH of a value ranging between 0 and 2 is increased to a value ranging between 3 and 3.5.

It has been found that in this manner, solutions having a high Al$_{13}$ content can easily be prepared. The scaling-up of processes in which the pH of solutions or suspensions is increased homogeneously to an industrial scale has often been effected during the development of deposition precipitation processes. For this purpose, many variants are available. Especially the increase of the pH of the solution in an electrochemical manner, as described in Europese patent 225659, is attractive for this.

The controlled enlargement of the dimensions of the polymeric complexes and the control of the chemical composition can also be carried out excellently by changing the pH or other concentrations in homogeneous solution. By precipitating (hydrated) metal oxides or hydroxides from homogeneous solution in the presence of suitable polymeric complexes, a deposition precipitation takes place wherein the dissolved metal ion is deposited on the complexes so as to be uniformly distributed. Here, particular reference is made to a process wherein first, through homogeneous increase of the pH value of an acid solution of aluminum ions, the formation of Al$_{13}$ polymers takes place. Then, through a further homogeneous increase of the pH level, other metal ions that only precipitate at higher pH values, are deposited on the Al$_3$ complexes. In general, it is possible to perform this process in one process step. In that case, an acid solution of aluminum ions and the other ions to be deposited on the Al$_{13}$ is started from, and the pH value of the solution is increased homogeneously to a level at which the other metal ions have also precipitated. The pillaring of clay minerals with such complexes also belongs to the invention, as well as clay minerals pillared with such complexes. The chemical reaction carried out is a reaction selected from the group of hydrocarbon cracking, isomerization, polymerization and hydration of olefins, the alkylation of aromatics and the dehydration of alcohols.

Preparation of Si/Al gel with Si/Al ratio of 5.67

Example 1

In a 250 ml beaker 100 ml demineralized water was added to 40.00 g water glass (approximately 27 wt. % SiO$_2$) and stirred vigorously.

An aluminate solution was prepared in another beaker (100 ml) by dissolving 11.90 g $Al(NO_3)_3 9H_2O$ in 80 ml 2M NaOH solution.

Then, with very vigorous stirring, the aluminate solution was poured into the water glass solution, whereupon a white gel was formed rather rapidly. This gel was XRD-amorphous and all Al was tetrahedrally coordinated ($^{27}Al$ MAS NMR)

Synthesis of Mg saponite from gel of Example 1

Example 2

In a precipitation vessel, as described by van Dillen et al (A. J. van Dillen, J. W. Geus, L. A. M. Hermans, J. van der Meyden, Proc. 6th Int. Conf. on Cat., 11 (5) 1977), the gel as prepared in Example 1 was suspended in 1.01 demineralized water with vigorous stirring and brought to 90° C.

Then, 40.67 g $Mg(NO_3)_2 6H_2O$ and 0.6M urea (36.04 g) were dissolved in 500 ml demineralized water, whereupon it was introduced into the precipitation vessel. The temperature was 90° C.; with continous stirring.

The first clay platelets were formed within some hours. After a reaction time of 20 hours, most of the gel had reacted to form small clay platelets of a length of 15–25 nm. A stacking was hardly (2 layers) present, if at all. The d(001) was absent at XRD measurements. The BET surface was 600–700 $m^2/g$ with a pore volume of approximately 0.3 ml/g.

Synthesis Al 13-pillars

Example 3

To 1L, 1 0M $Al(NO_3)_3 9H_2O$ (375.13 g) in demineralized water (90° C.), 1L, 3 0M urea (181.8 g) in demineralized water (50° C.) was added.

This reaction mixture was then brought to (and maintained at) 90° C. and stirred vigorously.

At the outset of the preparation, the Al-nitrate solution was first brought to pH 1. As a result of the decomposition of urea, the pH of the solution increased. This caused the aluminum to hydrolyze via different intermediate stages to the aluminum-13 (Al-13) complex. This can suitably be monitored with $^{27}Al$ NRM. In the range between pH 3 and 3.5 the amount of Al-13 is maximum (80%). After the formation of Al-13, the solution was stored as cool as possible to retard further hydrolysis.

Preparation of pillared saponite

Example 4

9 g clay, obtained according to Example 2, with zinc as octahedron ion, was suspended in approximately 150 ml demineralized water, enabling the clay to swell. In this manner, the cations in the interlayer of the clay became exchangeable.

After suspending for 2 hours, approximately 200 ml of the Al-13-containing solution (pH=3–3.5) described in Example 3 was added to the suspension and stirred for some hours (preferably overnight) with the exchange taking place.

After the exchange, the clay was allowed to settle down, whereupon the supernatant was decanted. The residue was washed with demineralized water. By means of centrifugation, the clay was separated from the rinse water and calcined for 4 hours at the desired temperature, preferably 350° C.

Synthesis of Ni-hectorite from amorphous silica

Example 5

In 1.5 L demineralized water 61.07 g $Ni(NO_3)_3 6H_2O$ was dissolved, whereupon this solution was acidified with $HNO_3$ to a pH of approximately 1.5.

To the above solution 9.653 g $LiNO_3$ was added with an excess of Li relative to Ni, with respect to the isomorphous substitution of Ni by Li. The atomic ratio Ni/Li in the synthesis mixture was $3/2$.

After dissolving, 11.4 g amorphous silica (aerosil 380V) was added to the solution and stirred vigorously (approximately 1500 rpm), with the temperature being brought to 90° C.

When the temperature of the suspension was 90° C., 37.84 g urea, together with 100 ml demineralized water, was added to the stirring solution. This point was the start of the synthesis (pH=2).

After 1.5 hour (pH=5.64), platelets (2.5 nm long) could already be seen around the large amount of amorphous material, while after 7 hours of synthesis (pH=5.54), nearly all gel had reacted to form platelets of 50 nm. Further extension of the synthesis period from 7 to 48 hours (pH=7.71) resulted in a further growth and stacking of the clay platelets (platelets of 75–150 nm).

Effects of administration of an amount of urea/lye Synthesis Zn saponite

The synthesis of Zn saponite can be performed in exactly the same manner as the Mg saponite synthesis mentioned in Example 2.

Example 6: Extra addition NaOH

In a precipitation vessel as described in Example 2, the gel as prepared in Example 1 was suspended in 1.01 demineralized water with vigorous stirring and brought to 90° C.

Then, 40.67 g $Mg(NO_3)_2 6H_2O$ and 0.6M urea (36.04 g) were dissolved in 500 ml demineralized water, whereupon it was introduced into the precipitation vessel. The temperature was 90° C.; with continuous stirring.

To the reaction mixture, NaOH was added until pH 8 was reached, whereupon the synthesis was started.

The first clay platelets were formed within some hours. After synthesis for 24 hours, a pH of 8.30 was reached, increasing only to 8.36 after a reaction period of 48 hours.

The stacking of the clay platelets, visible with TEM and XRD ((d(001)) was very great after a synthesis of 24 hours.

Example 7

An experiment was conducted similar to the process according to Example 2, the difference being that the amount of urea was doubled. After a synthesis of 24 hours, the pH was 7.73 (starting pH=5.50).

The stacking of the clay platelets was again very great, yet slightly less intense than in the case of Example 6.

Example 8

This reaction is comparable with Example 2, but now only half the amount of urea as applied in Example 2 was used. After a synthesis of 24 hours, the end pH was 7.05 (starting pH=5.25).

Example 9

This reaction is comparable with that of Example 8, but no urea was now added to the reaction mixture. After a synthesis of 24 hours, the end pH was 4.70 (starting pH=5.54).

Now, hardly any stacking was perceptible anymore with TEM. XRD no longer showed any stacking: the d(001) was absent.

Example 10. Friedel-Crafts alkylation of benzene with propene to form cumenes A saponite with Zn on the octahedron layer was prepared in the manner as described in Example 2. For this Zn saponite, the Si/Al ratio was 39.

After synthesis, the interlayer ions ($Na^+$) at this clay were exchanged for $Al^{3+}$, for application in the catalytic reaction.

After exchange, the clay was dried overnight at 120° C., whereupon a sieve fraction of from 0.1 to 0.4 mm was made. Next, 1.0 g saponite was dried under dry nitrogen for 3 hours at 120° C. and suspended in 444.2 g dry benzene (Janssen Chimica, 99.5% G.C.), without having been in contact with the air.

Hereafter, this benzene/saponite mixture was introduced into a 1 liter stainless steel autoclave, whereupon 35.3 g propene (HoekLoos) was added.

The total catalyst concentration was 0.2 wt. %. With continuous stirring, the autoclave was brought to a temperature of 160° C., at which the Friedel-Crafts alkylation of benzene with propene started. The pressure in the autoclave was 10.9 bar.

After 15 minutes reacting a sample was tapped and analysed by a gas chromatograph (GC Carlo Erba Instruments HRGC 5300, capillary column CP-Sil-CB).

Results after 15 minutes: Conversion: 87% with a selectivity to cumene of 74%. By-products were: Di- and Tri-isopropyl benzene.

Example 11, Friedel-Crafts alkylation of benzene with tetradecene to form phenyl tetradecene A saponite with Zn on the octahedron layer was prepared in the manner as described in Example 2. The Si/Al ratio for this Zn saponite was 39.

After synthesis, the interlayer ions ($Na^+$) at this clay were exchanged for $Al^{3+}$, for use in the catalytic reaction.

After exchange, the clay was dried overnight at 120° C., whereupon a sieve fraction of from 0.1 to 0.4 mm was made. Next, 5.0 g saponite was dried under dry nitrogen for 3 hours at 120° C. and put in 441.8 g dry benzene (Janssen Chimica, 99.5% G.C.), without having been in contact with the air. Hereafter, this benzene/saponite mixture was introduced into a 1 liter stainless steel autoclave, whereupon 137.1 g trans-7-tetradecene (Janssen Chimica, 92%) was added.

The total catalyst concentration was 0.8 wt. %. With continuous stirring, the autoclave was brought to a temperature of 180° C., at which the reaction started. The pressure in the autoclave was 8.5 bar.

After 15 minutes reacting, a sample was tapped and analysed by a gas chromatograph (GC Carlo Erba Instruments HRGC 5300, capillary column CP-Sil-CB).

Results after 15 minutes: Conversion: 62% with a selectivity to phenyltetradecene of 67%.

Example 12, Friedel-Crafts alkylation of benzene with benzyl chloride to form diphenylmethane A saponite with Mg in the octahedron layer was prepared in the manner as described in Example 2. The Si/Al ratio for this Mg saponite was 5.7.

After synthesis, the interlayer ions ($Na^+$) at this clay were not exchanged.

After synthesis, the clay was dried overnight at 120° C., whereupon a sieve fraction of from 0.1 to 0.4 mm was made.

Next, 2.0 g saponite was dried under dry nitrogen for 3 hours at 350° C. and put into 61.5 g dry benzene (Janssen Chimica, 99.5% G.C.), without having been in contact with the air.

Hereafter, this benzene/saponite mixture was introduced into a round-bottom flask, whereupon 7.7 g benzyl chloride (Janssen Chimica, 99.5% G.C.) was added.

The total catalyst concentration was 2.9 wt. %. With continuous stirring, the round-bottom flask was brought to a temperature of 84° C., at which the reaction started (reflux temperature).

After 1 hour reacting, a sample was tapped and analysed by a gas chromatograph (GC Carlo Erba Instruments HRGC 5300, capillary column CP-Sil-CB).

Results after 1 hour: Conversion: 42% with a selectivity to diphenylmethane of 98%.

What is claimed is:

1. Synthetic swelling clay minerals made up of a structure of elementary three-layer clay platelets consisting of a central layer of octahedrally oxygen-surrounded metal ions (octahedron layer), said layer being surrounded by two tetrahedrally surrounded, silicon atom-containing layers (tetrahedron layers), a number of such elementary platelets being optionally stacked, wherein the dimensions of said clay platelets vary from 0.01 μm to 1 μm, the number of the stacked elementary three-layer platelets varies from one platelet to twenty platelets, while in the octahedron layer at most 30 at. % of the metal ions has been replaced by ions of a lower valency, and in said tetrahedron layers at most 15at %of the silicon ions has been replaced by ions of a lower valency. such a replacement having taken place in at least one of said layers and said layers having a deficiency of positive charge because of the replacement.

2. Clay minerals according to claim 1, wherein in the octahedron layer, aluminum, chromium, iron(III), cobalt (III), manganese(III), gallium, vanadium, molybdene, tungsten, indium, rhodium and/or scandium are present as trivalent ions.

3. Clay minerals according to claim 1 wherein in the octahedron layer, magnesium, zinc, nickel, cobalt(II), iron (II), manganese(II), and/or beryllium are present as divalent ions.

4. Clay minerals according to claim 1, wherein in the octahedron layer, lithium is present as monovalent ions.

5. Clay minerals according to claim 1, wherein in the tetrahedron layer, silicon and/or germanium are present as tetravalent component and aluminum, boron, gallium, chromium, iron(III), cobalt(III) and/or manganese(III) are present as trivalent component.

6. Clay minerals according to any one of claim 1 wherein zinc and magnesium are incorporated into the octahedron layer, while the dimensions of the platelets are set by the choice of the magnesium and zinc ratio.

7. Clay minerals according to claim 1, wherein a part of the hydroxyl groups present in the platelets has been replaced by fluoride.

8. Clay minerals according to claim 1 wherein a surface area of at least 150 m² per gram is present in pores of at least 6 nm.

9. Clay minerals according to claim 1 wherein said clay minerals are pillared with oligomeric or polymeric hydroxy complexes of (metal) ions, such as aluminum, zinc, chromium and/or silicon.

10. A process for the preparation of clay minerals according to claim 1, wherein the pH of an aqueous liquid containing the components of the clay to be prepared is brought to a value of 3–9 and the temperature of the liquid is brought to a value of from 60 to 350° C. and maintained at said value for the time required for the reaction, said time not exceeding 25 hours, the pH being maintained at a value within said range.

11. A process according to claim 10, wherein solution of water glass and aluminate is started from, and said solution is brought, through acidification, to a pH where the metal ions to be incorporated into the clay structure are still soluble, and the pH of the thus obtained suspension is then increased homogeneously.

12. A process according to claim 10 wherein the dimensions of the elementary clay platelets are set by setting the temperature at which the pH is homogeneously increased between approximately 40 and 200° C.

13. A process according to claim 10 wherein the stacking of the elementary clay platelets is controlled by setting the ionic strength of the solution wherein the reaction leading to the clay minerals is carried out.

14. A process according to claim 10 wherein clay minerals having a high surface present in pores of great dimensions are obtained by carrying out the reaction leading to the clay minerals at a low ionic strength of the solution.

15. A process according to claim 10 wherein the elementary platelets are stacked to a high degree by setting the ionic strength of the solution from which the clay minerals are formed at a high value.

16. A process according to claim 10 wherein the pH of the solution is increased homogeneously through the disproportionation of sodium nitrite in the absence of oxygen.

17. A process according to claim 10 wherein the dimensions of the elementary clay layers are controlled within wide limits by setting the zinc/magnesium ratio.

18. A process according to claim 10 wherein substituting in the tetrahedron layer a controllable amount of silicon ions by aluminum ions through the addition of a basic aluminate solution to a suspension of silicon dioxide, then, through acidification, setting the pH at such a level that the metal ions to be incorporated into the octahedron layer are still soluble, then adding said metal ions, and then increasing the pH of the suspension homogeneously.

19. A process according to claim 10 for providing clay layers on a solid surface, wherein a high-porous layer of silicon dioxide which is strongly bonded to said surface is converted into clay minerals.

20. Solid surfaces covered with a clay layer, obtained by the use of the process according to claim 19 and having a thickness of from 1 to 10 $\mu$m.

21. Monoliths and stirring bodies according to claim 20, whose surfaces are covered with a clay layer.

22. A process for the preparation of oligomeric or polymeric hydroxy complexes of one or more metal ions of a narrow molecular weight distribution, suitable for use in the preparation of pillared clay minerals according to claim 9, wherein the pH of a solution of the metal ions is increased homogeneously.

23. A process for carrying out a chemical reaction in the presence of a heterogeneous catalyst, said reaction being catalyzed by a Lewis acid or a Brønsted acid, with a clay mineral according to being used as catalyst.

24. A process according to claim 23, the reaction being selected from the group of hydrocarbon cracking, isomerization, polymerization and hydration of olefins, the alkylation of aromatics and the dehydration of alcohols.

25. A process according to claim 23, the reaction being selected from the group consisting of Friedel-Crafts reactions and (hydro)cracking reactions.

26. A process according to claim 11, wherein the dimensions of the elementary clay platelets are set by setting the temperature at which the pH is homogeneously increased between approximately 40 and 200° C.

27. A process according to claim 26, wherein the stacking of the elementary clay platelets is controlled by setting the ionic strength of the solution wherein the reaction leading to the clay minerals is carried out.

28. A process according to claim 27, wherein clay minerals having a high surface present in pores of great dimensions are obtained by carrying out the reaction leading to the clay minerals at a low ionic strength of the solution.

29. A process according to claim 28, wherein the elementary platelets are stacked to a high degree by setting the ionic strength of the solution from which the clay minerals are formed at a high value.

30. A process according to claim 29, wherein the pH of the solution is increased homogeneously through the disproportionation of sodium nitrite in the absence of oxygen.

31. A process according to claim 30, wherein the dimensions of the elementary clay layers are controlled within wide limits by setting the zinc/magnesium ratio.

32. A process according to claim 31, wherein substituting in the tetrahedron layer a controllable amount of silicon ions by aluminum ions through the addition of a basic aluminate solution to a suspension of silicon dioxide, then, through acidification, setting the pH at such a level that the metal ions to be incorporated into the octahedron layer are still soluble, then adding said metal ions, and then increasing the pH of the suspension homogeneously.

33. A process according to claim 32 for providing clay layers on a solid surface, wherein a high-porous layer of silicon dioxide which is strongly bonded to said surface is converted into clay minerals.

34. A process according to claim 24, the reaction being selected from the group consisting of Friedel-Crafts reactions and (hydro)cracking reactions.

35. Synthetic swelling clay minerals made up of elementary three-layer platelets consisting of a central layer of octahedrally oxygen-surrounded metal ions (octahedron layer), said layer being surrounded by two tetrahedrally surrounded, silicon atom-containing layers (tetrahedron layers), a number of such elementary platelets being optionally stacked, wherein a) the dimensions of said platelets vary from 0.01 $\mu$m to 1 $\mu$m;

b) the number of said stacked elementary three-layer platelets varies from one platelet to twenty platelets, while in said octahedron layer at most 30 at. % of the metal ions has been replaced by ions of a lower valency and in said tetrahedron layers at most 15 at. % of the silicon ions has been replaced by ions of a lower valency, such a replacement having taken place in at least one of said layers and said layers having a deficiency of positive charge because of the replacement;

c) in said octahedron layer, magnesium, zinc, nickel, cobalt (II), iron (II), manganese (II), and/or beryllium are present as divalent ions; and lithium is present as monovalent ions;

d) in said tetrahedron layer, silicon and/or germanium are present as tetravalent component and aluminum, boron, gallium, chromium, iron (III), cobalt (III) and/or manganese (III) are present as trivalent component;

e) in that a part of the hydroxyl groups present in said platelets has been replaced by fluorine;

f) in that a surface area of at least 150 m² per gram is present in pores of at least 6 nm; and g) in that said clay minerals are pillared with oligomeric or polymeric hydroxy complexes of (metal) ions, such as aluminum, zinc, chromium and/or silicon.

36. The synthetic swelling clay minerals of claim 35, wherein in said octahedron layer, substantially magnesium and zinc are present as divalent ions; while the dimensions of the platelets are set by the choice of the magnesium and zinc ratio.

37. Clay minerals according to claim 8, in which said clay minerals have a structure in which there is hardly any or no reflections in the 001 plane as determined by x-ray diffraction.

38. Solid surfaces covered with a clay layer, obtained by the use of the process according to claim 19 and having a thickness of from 1 to 5 μm.

39. Solid surfaces covered with a clay layer, obtained by the use of the process according to claim 19 and having a thickness of from 2 to 3 μm.

* * * * *

UNITED STATES PATENT AND TRADEMARK OFFICE
CERTIFICATE OF CORRECTION

PATENT NO. : 6,187,710 B1
DATED : February 13, 2001
INVENTOR(S) : Roland Jacobus Martinus Josephus Vogels et al.

It is certified that error appears in the above-identified patent and that said Letters Patent is hereby corrected as shown below:

Column 12,
Line 53, "$Al_3$" should read -- $Al_{13}$ --;

Column 16,
Line 52, "to any one of claim 1" should read -- to claim 1 --; and

Column 17,
Line 60, "to being" should read -- to claim 1 --.

Signed and Sealed this

Twenty-seventh Day of August, 2002

Attest:

Attesting Officer

JAMES E. ROGAN
Director of the United States Patent and Trademark Office